US00PP36901P3

(12) United States Plant Patent
Schoone

(10) Patent No.: US PP36,901 P3
(45) Date of Patent: Aug. 26, 2025

(54) ***PHALAENOPSIS* PLANT NAMED 'Sister Sunshine'**

(50) Latin Name: *Phalaenopsis hybrida*
Varietal Denomination: Sister Sunshine

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/735,122

(22) Filed: Jun. 5, 2024

(65) Prior Publication Data

US 2024/0415039 P1 Dec. 12, 2024

Related U.S. Application Data

(60) Provisional application No. 63/471,471, filed on Jun. 6, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Sister Sunshine', characterized by its upright plant habit; moderately vigorous to vigorous growth habit; strong flowering stems; strong leaves; freely flowering habit with typically two inflorescences developing per plant, each inflorescence with numerous flowers; flowers with greenish yellow-colored petals and sepals; and good postproduction longevity.

2 Drawing Sheets

Figure 1:
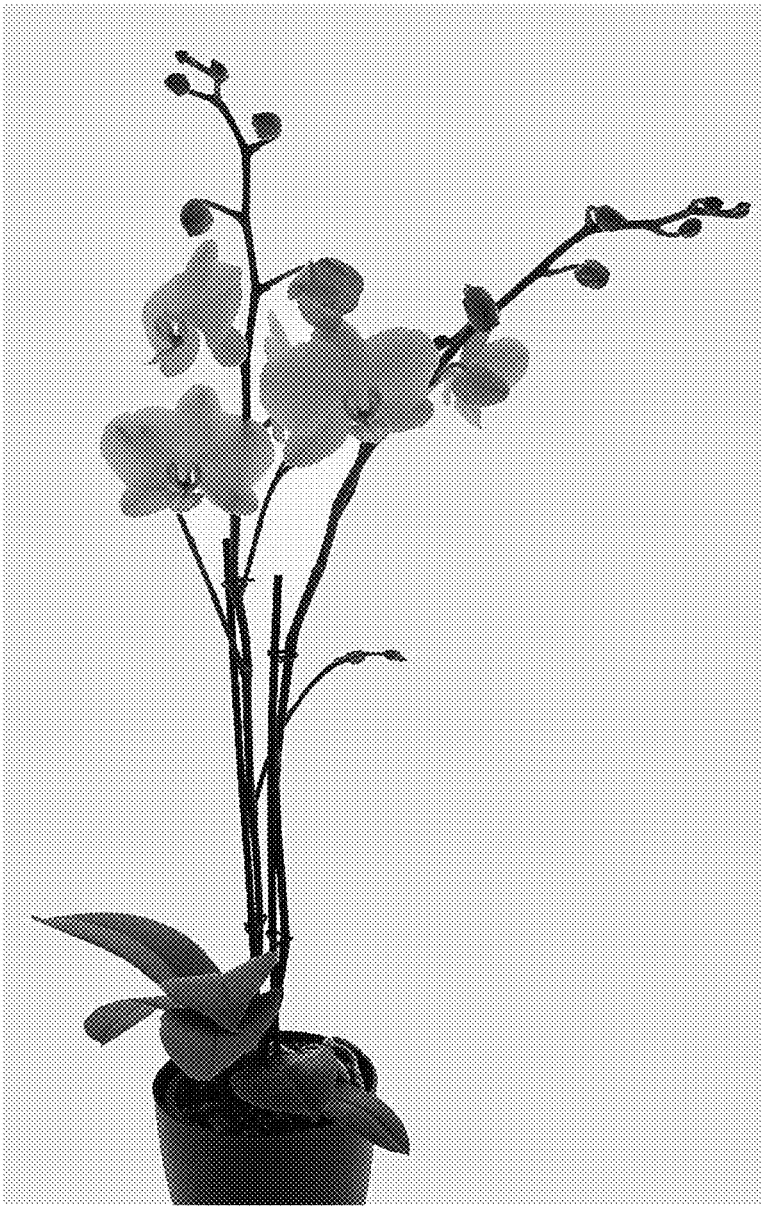

Botanical designation: *Phalaenopsis hybrida.*
Cultivar denomination: 'SISTER SUNSHINE'.

CROSS-REFERENCED TO CLOSELY-RELATED APPLICATIONS

Title: Varieties of *Phalaenopsis* Plants
Inventor: René Schoone
Filed: Jun. 6, 2023
Ser. No. 63/471,471
Inventor and Applicant/Assignee hereby claims the benefit of this provisional U.S. Patent Application.

STATEMENT REGARDING PRIOR DISCLOSURES BY INVENTOR and APPLICANT/ASSIGNEE

A European Community Plant Breeder's Rights application for the instant plant was filed by the Applicant/Assignee of the instant application, Floricultura B.V. of Heemskerk, The Netherlands on May 5, 2023, application number 2023/0978. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Sister Sunshine'.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January 2013 in Assendelft, The Netherlands of *Phalaenopsis hybrida* 'Fuller's Sunset', not patented, as the female, or seed, parent with *Phalaenopsis hybrida* 'Gan Lin Diamond', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November 2019.

Asexual reproduction of the new *Phalaenopsis* plant by in vitro meristem propagation in a controlled environment in Assendelft, The Netherlands since December 2020 has shown that the unique features of this new *Phalaenopsis* plant are stable and reproduced true to type in successive generations.

The following traits have been repeatedly observed and are determined to be the unique characteristics of 'Sister Sunshine'. These characteristics in combination distinguish 'Sister Sunshine' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences developing per plant, each inflorescence with numerous flowers.
6. Flowers with greenish yellow-colored petals and sepals.
7. Good postproduction longevity.

Plants of the new *Phalaenopsis* can be compared to plants of the female parent, 'Fuller's Sunset'. Plants of the new *Phalaenopsis* differ primarily from plants of 'Fuller's Sunset' in flower color as petals and sepals of plants of the new *Phalaenopsis* are greenish yellow in color whereas petals and sepals of plants of 'Fuller's Sunset' are purplish red in color.

Plants of the new *Phalaenopsis* can be compared to plants of the male parent, 'Gan Lin Diamond'. Plants of the new *Phalaenopsis* differ primarily from plants of 'Gan Lin Diamond' in flower color as petals and sepals of plants of the new *Phalaenopsis* are greenish yellow in color whereas petals and sepals of plants of 'Gan Lin Diamond' are purplish red in color.

Plants of the new *Phalaenopsis* can be compared to plants of *Phalaenopsis hybrida* 'Mirage', not patented. In side-by-side comparisons, plants of the new *Phalaenopsis* differ primarily from plants of 'Mirage' in plant size as plants of the new *Phalaenopsis* are shorter than plants of 'Mirage'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Sister Sunshine' grown in a container.

Figure 2:
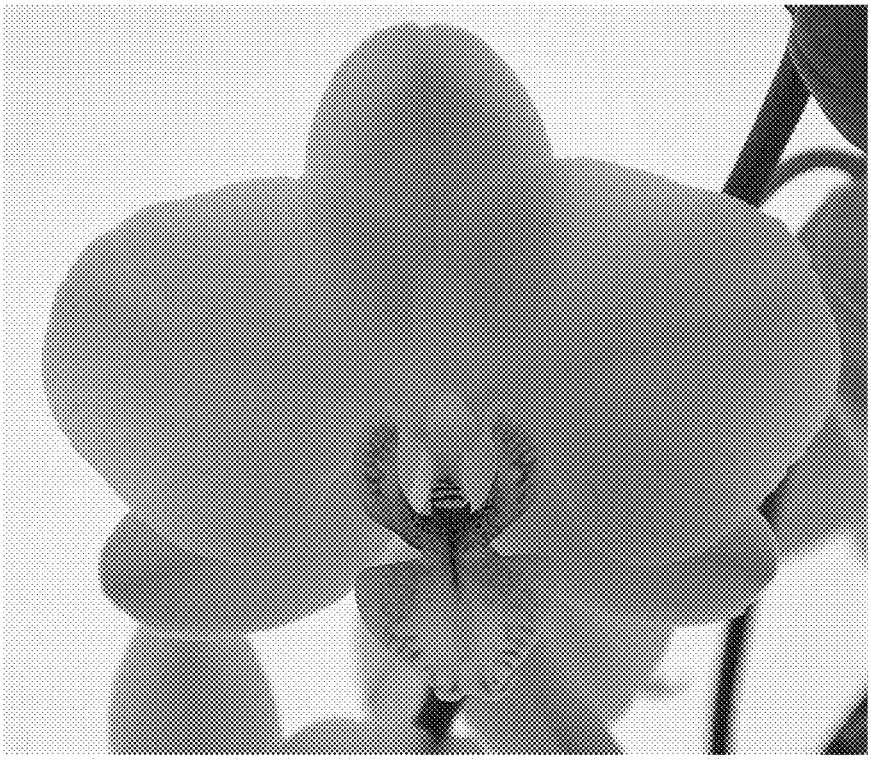

The photograph on the second sheet (FIG. 2) is a close-up view of a typical flower of 'Sister Sunshine'.

DETAILED BOTANICAL DESCRIPTION

The aforementioned photographs and following observations and measurements describe plants grown during the late winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Sister Sunshine'.

Parentage:

*Female, or seed, parent.*—*Phalaenopsis hybrida* 'Fuller's Sunset', not patented.

*Male, or pollen, parent.*—*Phalaenopsis hybrida* 'Gan Lin Diamond', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane.*—About 12.6 cm.

*Plant height, substrate level to top of floral plane.*—About 45.3 cm.

*Plant diameter or spread.*—About 34 cm.

Leaf description:

*Arrangement and quantity.*—Distichous, simple; sessile; about six fully-developed leaves per plant.

*Length.*—About 17 cm.

*Width.*—About 6.2 cm.

*Aspect.*—Semi-erect to somewhat outwardly arching.

*Shape.*—Elliptic to elliptic-oblong; slightly carinate.

*Apex.*—Unequal acute.

*Base.*—Sheathing. Sheath length: About 1.6 cm. Sheath width: About 1.2 cm. Sheath color, upper and lower surfaces: Close to a blend of 143A and 144A; towards the margins, tinged with close to 200B and 200C.

*Margin.*—Entire.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to a blend of NN137A and NN137B; towards the base, tinged with close to N199B. Developing leaves, lower surface: Close to 146A; strongly tinged with close to 200A. Fully expanded leaves, upper surface:

Close to NN137B; narrow marginal edges, close to 143B; venation, close to 139A. Fully expanded leaves, lower surface: Close to 146A; towards the apex and margins, slightly tinged with close to N199A; venation, close to 200B.

Inflorescence description:

*Appearance and flowering habit.*—Showy zygomorphic flowers arranged on axillary simple or branched racemes; typically two inflorescences develop per plant; each inflorescence with about 13 flowers; flowers face outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 33.1 cm.

*Inflorescence width.*—About 14.4 cm.

*Flower buds, about one week before opening.*—Height: About 2.1 cm. Diameter: About 1.5 cm. Shape: Broadly ovate. Color: Close to 144A and 144B variably tinged with close to 176B.

*Flower size.*—About 8.1 cm (vertical) by 9.1 cm (horizontal).

*Flower depth.*—About 3.8 cm.

*Petals, quantity and arrangement.*—Three, two lateral petals and one center petal transformed into a labellum.

*Lateral petals.*—Length: About 4.3 cm. Width: About 5.1 cm. Shape: Reniform to broadly reniform-ovate; slightly concave. Apex: Obtuse. Margin: Entire; slightly undulate. Texture and luster, upper and lower surfaces: Smooth, glabrous; moderately velvety; matte. Color: When opening, upper surface: Close to 150C; towards the base, close to 145C; fine veins, close to 177D. When opening, lower surface: Close to a blend of 145C and 150C; towards the margins, close to 154D; towards the base, close to 145C; fine veins, close to 177D. Fully opened, upper surface: Close to 2C; towards the apex, close to 1D; towards the base, close to 145D; fine veins, close to 165C; colors do not change with subsequent development. Fully opened, lower surface: Close to a blend of 154C and 154D; towards the margins, close to 3C and 3D; towards the base, close to 145B to 145C; colors do not change with subsequent development.

*Labella.*—Appearance: Three-parted with two lateral lobes and a central lobe. Length, lateral lobes: About 1.8 cm. Width, lateral lobes: About 1 cm. Length, central lobe: About 2.5 cm. Width, central lobe: About 0.6 cm to 2.3 cm. Length, cirrhose tips: About 7 mm. Shape, lateral lobes: Obovate. Shape, central lobe: Deltoid with a slightly elongated apex. Apex, lateral lobes: Obtuse. Apex, central lobe: Cleft with two upright curled cirrhose tips. Margins, lateral lobes: Entire. Texture and luster, lateral and central lobes, upper and lower surfaces: Smooth, glabrous, moderately velvety; matte. Callosities: Located at the base of the labellum and attachment point of the lateral petals; about 4.5 mm in length, about 4 mm in width and about 4 mm in height. Color: When opening, upper surface: Lateral lobes: Close to NN155D; towards the proximal margins, close to 5B and 5C; towards the base, close to 181A; axial stripes, close to 181C; venation, close to 181C. Central lobe: Close to 1B; towards the apex, close to NN155B; center, close to 154B; at the base, close to NN155B; narrow marginal edges, close to 164A; radial stripes, close to 185A; cirrhose tips, close to NN155B with axial stripes, close to 185D; venation, close to 182B. When opening, lower surface: Lateral lobes: Close to 182D; center, close to 158D; towards the proximal margins, close to 5A. Central lobe: Close to a blend of 150C and 154C; towards the apex, close to NN155B; at the base, close to 156B to 156D; narrow marginal edges, close to 164A; fine veins, close to 165C; cirrhose tips, close to NN155B. Fully opened, upper surface: Lateral lobes: Close to NN155B; towards the proximal margins, close to 13B and 13C; towards the base, close to 178A; axial stripes, close to 178D. Central lobe: Close to a blend of 1A and 3A; towards the apex, close to NN155A; center, close to 6A; towards the base, close to NN155B and at the base, close to 4C; narrow marginal edges, close to 178A; radial stripes, close to 185A; cirrhose tips, close to NN155A with axial stripes, close to 185D. Fully opened, lower surface: Lateral lobes: Close to 182D; center, close to 158D; towards the proximal margins, close to 13A. Central lobe: Close to 155A; towards the apex, close to NN155B; towards the margins, close to a blend of 151D and 154B with fine veins, close to 165C; at the base, close to 156B to 156C; narrow marginal edges, close to 178A; cirrhose tips, close to NN155B. Callosities: When developing: Close to 4C; towards the apex, close to 4A with fine dots, close to 185A and at the apex, close to 13A with fine dots and stripes, close to 185A. Fully developed: Close to 12A; towards the apex, fine dots, close to 185A and at the apex, close to 17B with fine dots and stripes, close to 185A.

*Sepals.*—Quantity and arrangement: Three, one upper dorsal sepal and two lower lateral sepals. Length, dorsal sepal: About 4.5 cm. Width, dorsal sepal: About 3 cm. Length, lateral sepals: About 4.4 cm. Width, lateral sepals: About 2.6 cm. Shape, dorsal sepal: Obovate. Shape, lateral sepals: Ovate. Apex, dorsal sepal: Shallowly emarginate. Apex, lateral sepals: Obtuse. Base, dorsal sepal: Broadly cuneate. Base, lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 150C; towards the apex, close to a blend of 145D and 150C; fine veins, close to N199A. When opening, lower surface: Close to N144D slightly tinged with close to 177C; distal margins, close to 150B. Fully opened, upper surface: Close to a blend of 150C and 154C; towards the base, close to 145D; distal margins, close to 154D; fine veins, close to 152D. Fully opened, lower surface: Close to a blend of 145C and 150B slightly tinged with close to 177C; distal margins, close to 154D. Color, lateral sepals:

When opening, upper surface: Close to 150C; towards the base, close to 150B and at the base, a few fine dots, close to 178A; fine veins, close to N199A. When opening, lower surface: Close to N144D venation, close to 146C and 146D. Fully opened, upper surface: Close to 150C; towards the apex and margins, close to 154C and 154D; towards the base, close to 145D and at the base, a few fine dots, close to 178B. Fully opened, lower surface: Close to a blend of 145B and 150B; towards the apex and margins, close to a blend of 150C and 154C; venation, close to 145A.

*Peduncles.*—Length: About 56 cm. Diameter: About 5 mm. Strength: Strong. Aspect: Upright to outwardly arching. Texture and luster: Smooth, glabrous; matte. Color: Close to 200A heavily covered with fine dots, close to 147C.

*Pedicels.*—Length: About 4.1 cm. Diameter: About 3 mm. Strength: Moderately strong. Aspect: About 55° from peduncle axis. Texture and luster: Smooth, glabrous; matte. Color: Close to 145A; proximally, close to 148A and distally, close to 151D.

*Reproductive organs.*—Androecium: Column length: About 1 cm. Column width: About 5.5 mm. Column color: Close to NN155A. Pollinia quantity: Two. Pollinia diameter (per two pollinia): About 2.5 mm. Pollinia color: Close to 21A. Gynoecium: Stigma length: About 3.5 mm. Stigma width: About 4 mm. Stigma shape: Reniform. Stigma color: Close to N155A. Ovary length: About 8 mm. Ovary diameter: About 1 mm. Ovary color: Close to 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Sister Sunshine' as herein illustrated and described.

* * * * *